United States Patent [19]

Ryu

[11] 4,110,410

[45] Aug. 29, 1978

[54] OLIGOMERIZATION OF OLEFINS

[75] Inventor: Ji-Yong Ryu, Des Plaines, Ill.

[73] Assignee: UOP Inc., Des Plaines, Ill.

[21] Appl. No.: 808,932

[22] Filed: Jun. 22, 1977

Related U.S. Application Data

[63] Continuation-in-part of Ser. No. 645,118, Dec. 29, 1975, Pat. No. 4,048,109.

[51] Int. Cl.$^2$ .............................................. C07C 3/18
[52] U.S. Cl. ........................................... 260/683.15 B
[58] Field of Search ................................ 260/683.15 B

[56] References Cited

U.S. PATENT DOCUMENTS 3,193,596   7/1965   Bown et al. ................. 260/683.15 B

*Primary Examiner*—C. Davis
*Attorney, Agent, or Firm*—James R. Hoatson, Jr.; Raymond H. Nelson; William H. Page, II

[57] ABSTRACT

Olefinic hydrocarbons containing from 2 to about 6 carbon atoms are oligomerized by treatment with a heterogeneous oligomerization catalyst which has been prepared by heating a metal oxide, thereafter contacting the metal oxide with titanium tetrachloride vapor in a series of steps at progressively higher temperatures ranging from about 50° to about 600° C. and thereafter heating the impregnated metal oxide in contact with hydrogen gas at an elevated temperature in the range of from about 300° to about 700° C. to reduce the titanium to a valence state of less than +4.

10 Claims, No Drawings

OLIGOMERIZATION OF OLEFINS

CROSS-REFERENCE TO RELATED APPLICATIONS

This application is a continuation-in-part of my co-pending application Ser. No. 645,118 filed Dec. 29, 1975, now U.S. Pat. No. 4,048,109, Sept 13, 1977, all teachings of which are specifically incorporated herein by reference thereto.

BACKGROUND OF THE INVENTION

Heretofore, the prior art has disclosed catalysts for the polymerization of olefins, said catalysts comprising those known in the art as Ziegler-Natta catalysts. These catalysts typically consist of titanium tetrachloride which has been activated with an aluminum alkyl and operate in the form of a sludge or slurry. For example U.S. Pat. 2,945,845 discloses a titanium tetrachloride catalyst which is used in conjunction with an organic compound such as triethyl aluminum or U.S. Pat. Nos. 3,660,419 and 3,725,497 which also teach the use of titanium tetrachloride catalysts which have been activated with the organoaluminum compounds. Titanium tetrachloride is reduced to lower valent titanium chloride by the aluminum alkyl. Other titanium halide catalysts which have been disclosed in the prior art include those such as shown in U.S. Pat. No. 3,153,634 in which a titanium tetrahalide is impregnated on an alumina such as gamma-alumina and is thereafter subjected to reducing conditions such as by treatment with hydrogen at temperatures ranging from 250° C. to 500° C. Alternatively, the impregnated alumina could be reduced by contact with a solution or dispersion of a reducing agent such as the alkali or alkaline earth metals or metal hydrides, etc. However, the catalysts thus prepared are useful in polymerizing olefins to form solid polymers, and specifically, high molecular weight solid polymers in which the molecular weight will range from 300 to 100,000. In addition to describing the preparation of solid polymers, this patent also states that aromatic hydrocarbons such as benzene, toluene, xylene or ethers may be used as suitable diluents. However, this is in contradistinction to the heterogeneous oligomerization catalyst of the type hereinafter set forth in greater detail in which it has been found that it is not possible to utilize aromatic hydrocarbons as diluents inasmuch as the olefinic hydrocarbon, if present, would enter into the reaction in which the olefin would act as an alkylating agent rather than as a monomer in a polymerization reaction.

Another prior art patent, namely, U.S. Pat. No. 2,965,686, discloses a catalyst which is prepared by activating alumina by evacuation at a temperature of 600° C. for a period ranging from about 18 hours to about 21.5 hours. After activation of the alumina, the base was then treated with a mixture of argon, an inert gas, and titanium tetrachloride vapor at a temperature of about 600° C. for an unspecified period of time. The resultant catalyst was then used in an alkylation reaction for the propylation of cumene to form diisopropylbenzene. This patent is silent as to the type of alumina which was used as the base for the catalyst. In the process of the present invention, as will hereinafter be set forth in greater detail, it is believed that the substrate or base which is utilized must possess surface hydroxyl groups and therefore it is necessary to use specific type of alumina such as gamma-alumina, eta-alumina, etc. Another prior art reference which discloses polymerization catalysts in U.S. Pat. No. 3,506,633 which teaches polymerization catalysts having a chlorine:titanium ratio of 2.5 to 3.5. However, in contradistinction to the catalyst of the present invention, this catalyst is used to prepare solid polymers. Yet another prior patent in this field is U.S. Pat. No. 2,381,481 in which the preparation and use of a catalyst prepared by treating alumina gel with fluotitanic acid is disclosed. However, as is the case of the previously mentioned patents, this catalyst is used to polymerize olefins to heavier hydrocarbons, i.e., solid polymers and is also used to alkylate paraffins with olefins, usually at temperatures ranging between 700° C. and 900° F. or higher. U.S. Pat. No. 2,951,885 discloses a titanium trihalide on an activated alumina or other activated acidic oxides. However, the catalyst is originally a tetrahalide which is subsequently reduced to a trihalide with an alkali metal such as sodium, potassium or lithium and used to alkylate benzene with olefins rather than for the oligomerization of olefins containing from 2 to about 6 carbon atoms.

It has been known that Lewis acids such as metal halides can catalyze the Friedel-Crafts type reactions and since Lewis acid alone shows no or only mild catalytic activity, Lewis acids normally require cocatalyst. Titanium tetrahalides are well known Lewis acid. (Reference: A. G. Evans, G. W. Meadows and M. Polanyi; Nature (London), 158, 94 (1946)).

As will hereinafter be set forth in greater detail, I have now discovered that olefinic hydrocarbons containing either terminal or internal olefinic double bonds may be oligomerized by treatment with a heterogeneous oligomerization catalyst which is prepared by reducing titanium tetrachloride supported on a metal oxide which possesses surface hydroxyl groups and preferably a Group IIIA metal oxide with hydrogen gas in a series of steps which involves utilizing progressively higher temperatures during the reduction process whereby the catalyst which is produced will give entirely different results when used in treating these olefinic hydrocarbons than have been obtained when utilizing catalysts of the prior art.

SPECIFICATION

This invention relates to a process for the oligomerization of olefinic hydrocarbons. More specifically the invention is concerned with a process for the oligomerization of olefinic hydrocarbons utilizing, as a catalyst therefor, a composite which has been prepared by treating an activated metal oxide which possesses surface hydroxyl groups with titanium tetrachloride, thereafter heating the resulting composite and reducing in the presence of hydrogen gas whereby the resultant catalyst system contains titanium which is present in a valence state of less than +4.

Many olefinic hydrocarbons which contain from 6 to about 8 carbon atoms in the chain are utilized in industry in many ways. For example, one specific use of these hydrocarbons, and especially hydrocarbons containing 8 carbon atoms in the chain, is as a component in motor fuel whereby the octane number of the fuel may be improved to a higher level, the presence of these hydrocarbons enabling the motor fuel such as gasoline to possess a relatively high octane number either in the leaded or unleaded state. Another use of hydrocarbons containing the aforementioned number of carbon atoms in the chain would be as starting materials for the preparation of plasticizers.

It is therefore an object of this invention to provide a process for the oligomerization of olefinic hydrocarbons.

A further object of this invention is to provide a process for the oligomerization of olefinic hydrocarbons utilizing a catalyst system comprising a titanium chloride-Group IIIA metal oxide support in which the titanium is present in a valence state of less than +4.

In one aspect an embodiment of this invention resides in a process for the oligomerization of an olefinic hydrocarbon which contains from 2 to about 6 carbon atoms which comprises oligomerizing said hydrocarbon at oligomerization conditions in the presence of a catalyst which has been prepared by heating a metal oxide which possesses surface hydroxyl groups at a temperature in the range of from about 400° C. to about 600° C., contacting said metal oxide with titanium tetrachloride vapor in a series of steps at progressively higher temperatures within the range of from about 50° C. to about 600° C. to deposit titanium tetrachloride on the metal oxide, and thereafter heating the impregnated metal oxide in contact with hydrogen gas at a temperature in the range of from about 300° C. to about 700° C. to reduce the titanium to a valence state of less than +4, and recovering the resultant oligomer.

A specific embodiment of this invention is found in a process for the oligomerization of an olefinic hydrocarbon which comprises oligomerizing ethylene at a temperature in the range of from about ambient to about 250° C. and a pressure in the range of from about atmospheric to about 100 atmospheres in the presence of a catalyst which is prepared by heating a low density, high surface area gamma-alumina at a temperature in the range of from about 400° C. to about 600° C., contacting said alumina with titanium tetrachloride in a series of steps at progressively higher temperatures within the range of from about 50° C. to about 600° C. to deposit titanium tetrachloride on the gamma-alumina, thereafter heating the titanium tetrachloride impregnated gamma-alumina in contact with hydrogen gas at a temperature in the range of from about 300° C. to about 700° C. to reduce the titanium to a valence state of less than +4, and recovering the resultant oligomer.

Other objects and embodiments will be found in the following further detailed description of the present invention.

As hereinbefore set forth the present invention is concerned with a process for the oligomerization of olefinic hydrocarbons in which the process is effected in the presence of certain catalytic compositions of matter hereinafter described in greater detail. The term "polymerization" has a relatively broad meaning in the chemical art. Although, it is generally referred to as the preparation of relatively high molecular weight polymers, it may also refer to low molecular weight polymers. In contradistinction to this, the term "oligomerization" refers to polymeric compounds in which the molecule consists of only a relatively few monomer units and would include dimerization, trimerization, or tetramerization. In view of the unpredictable art of catalysis, it was totally unexpected that catalytic compositions of matter which are prepared in a certain manner hereinafter set forth in greater detail would, when used in the treatment of olefinic hydrocarbons, result in the oligomerization of these olefins. For example, one catalyst of the prior art previously discussed was prepared by passing vapor or nitrogen-titanium tetrachloride vapor over a gamma-alumina at a temperature in the range of from about 500° C. to about 900° C. and thereafter reducing with hydrogen gas at temperatures ranging from 250° C. to 500° C., the finished catalysts containing from 1 to 10% by weight of titanium trichloride. These catalysts, when used to polymerize olefins, produced solid products possessing molecular weights from 300 to 100,000 when using reaction conditions which included temperatures ranging from 50° C. to 100° C., pressures ranging from 14.7 to 500 psig and liquid hourly space velocities ranging from 0.1 to 10. However, these catalytic compositions of matter were used to polymerize only terminal olefinic hydrocarbons as contrasted to the catalyst of the present invention which can oligomerize both internal and terminal olefins.

Olefinic hydrocarbons which may be oligomerized according to the process of this invention will comprise those olefins containing from 2 to about 6 carbon atoms such as ethylene, propylene, 1-butene, 2-butene, 1-pentene, 2-pentene, 1-hexene, 2-hexene, 3-hexene and branched chain isomers thereof.

The heterogeneous oligomerization catalyst of the present invention comprises titanium tetrachloride composited on an activated metal oxide which possesses surface hydroxyl groups. Specific examples of these metal oxides will include Group IIIA metal oxides which possess surface hydroxyl groups and which also possess a relatively high surface area such as alumina, gallium oxide, indium oxide and thallium oxide. In the preferred embodiment, the substrate comprises alumina, and in particular, the alumina substrate which is employed will constitute a low density, high surface area alumina such as gamma-alumina or, if so desired, eta-alumina. The apparent bulk density of the alumina may range from about 0.3 to about 0.7 g/cm$^3$ or higher with a surface area ranging from about 1 to about 500 m$^2$/g. The alumina may be in any shape, one example of the substrate being spheroidal alumina which is prepared by the conventional and commercial oil-drop method as described in U.S. Pat. No. 2,620,314. In addition, it is also contemplated within the scope of this invention that the alumina may be treated to provide greater physical stability, one type of treatment being to impregnate the gamma-alumina with a compound such as barium nitrate which, upon calcination, is converted into barium oxide. The latter compound will then, as hereinbefore set forth, provide greater physical stability for the alumina. It is also contemplated within the scope of this invention that a commercial gamma-alumina may also be used as the support. However, since this commercial gamma-alumina could contain an excessive amount of water which would consume an excess of titanium tetrachloride without any beneficial effect on the catalyst, in the preferred embodiment of this invention, the commercial gamma-alumina is subjected to a predrying step by heating to a temperature in the range of from about 400° C. to about 600° C. under an inert gas or hydrogen flow for a period of about 1 to about 8 hours.

In order to achieve the maximum activity of the metal oxide support, it is necessary to avoid severe drying of said support. For example, the drying of alumina at temperatures in excess of about 600° C., such as 650° C., will seriously deplete the alumina of the hydroxyl groups present thereon. This severe drying step will not only remove the water which is absorbed on the alumina, but will also remove the aforesaid surface hydroxyl groups which are essential to make an active catalyst, said surface hydroxyl groups reacting with the titanium component of the titanium tetrachloride.

The gamma-alumina which is then predried is then placed in an appropriate apparatus which may comprise a flask, tube etc., and a gas mixture of hydrogen or nitrogen and titanium tetrachloride which has been prepared by bubbling hydrogen gas or nitrogen gas through the liquid titanium tetrachloride at room temperature is passed over the gamma-alumina in a series of stepwise treatments at an elevated temperature which may range from about 50° C. up to about 600° C. or more. The passage of the hydrogen- or nitrogen-titanium tetrachloride mixture over the alumina is effected for a period of time which may range from about 0.5 up to about 3 hours or more in duration, the amount of time being dependent upon the amount of gamma-alumina which is present and the flow rate of the titanium tetrachloride-hydrogen or nitrogen gas mixture. In the preferred embodiment of the invention, the titanium tetrachloride in the gaseous mixture is first passed over the support at a temperature of about 140° C. for a period of about 3 hours. The temperature of the flask is then raised to about 300° C. for an additional period of 1 hour and thereafter the catalyst is then heated to a temperature in excess of 300° C. up to about 700° C. and subjected to a flow of hydrogen gas for a period of 3 hours. The preferred temperature for the heat treatment of this resulting composite is from about 135° C. to about 550° C., however, it will be dependent on the oligomerization temperature which is used in the oligomerization process. Generally, it is preferred that the temperature which is used in the treatment of the composite be equal to, or higher than, the oligomerization temperature. At the end of this time, the finished catalyst is then sealed under an inert atmosphere prior to the use thereof, said inert atmosphere comprising gases such as argon, helium, nitrogen, etc.

Alternatively, the catalyst composite or system as utilized in the process of the present invention may be prepared by forming a solution of titanium tetrachloride in a polar non-aqueous organic solvent and thereafter impregnating the substrate such as gamma-alumina with the organic solution. The thus impregnated substrate is then dried to remove the solvent and is thereafter treated with hydrogen in a manner similar to that hereinbefore set forth to reduce the titanium to a valence state of less than +4. Upon completion of the final treatment the finished catalyst system is then sealed under an inert atmosphere.

While the aforesaid discussion has been centered upon the use of gamma-alumina as a substrate for the reduced titanium chloride, it is also contemplated that other Group IIIA metal oxides which possess surface hydroxyl groups and which also possess a relatively high surface area such as gallium oxide, indium oxide and thallium oxide may also be used. However, of these compounds, the preferred substrate is alumina, and especially low density, high surface area aluminas such as gamma-alumina or, if so desired, eta-alumina.

It is also contemplated within the scope of this invention that the catalyst system hereinbefore described may be composited on a solid support. The preferred solid supports which may be utilized comprise high surface area inert compounds, some representative examples of which will include silica or mixtures of silica with other inorganic oxides such as silica-magnesia, silica-zironia, silica-thoria, silica-magnesia-zirconia, etc.; charcoal, coal, diatomaceous earths and clays, such as fuller's earth, bentonite, montmorillonite, kieselguhr, etc. It is to be understood that these compounds will act only as supports for the catalyst system and will not enter into the catalytic activity of the composite. The titanium chloride in a reduced state of less than +4 and Group IIIA metal oxide catalyst may be composited on the aforesaid inert supports in any manner known in the art such as by impregnation, deposition, etc.

In addition, it is also to be considered within the scope of this invention that one or more promoters may be added to the catalyst system. It is believed that use of one or more promoters selected from the metals of Group VIB or Group VIII of the Periodic Table may be beneficial to the practice of the present invention.

The catalysts thus prepared according to the method hereinbefore set forth are then used to oligomerize olefinic hydrocarbons containing from 2 to about 6 carbon atoms, the greatest yield of products comprising dimers and trimers of the monomeric olefin. The polymerization of said olefins is effected in a conventional manner, that is, by placing the titanium chloride-alumina catalyst in which the titanium is present in a valence state lower than +4 in an appropriate apparatus which may comprise a reaction flask, autoclave, etc. It is to be understood that the placement of the catalyst is effected while maintaining said catalyst in an inert atmosphere, said atmosphere comprising, as hereinbefore set forth, argon, nitrogen, helium, etc. Thereafter the olefinic hydrocarbon which is to be oligomerized is charged to the reaction vessel containing the catalyst at predetermined reaction conditions which may include temperatures ranging from about ambient (about 20°–25° C.) to about 250° C., pressures ranging from atmospheric to about 100 atmospheres or more and liquid hourly space velocities ranging from about 1 to about 10. It is contemplated within the scope of this invention that the olefins which are to be oligomerized may be admixed with paraffins which will act as diluents for the reaction. However, in contradistinction to the prior art, the olefins may not be admixed with an aromatic diluent, unless said aromatic compound is highly alkylated, inasmuch as the aromatic diluent in an unsubstituted form will interfere with the reaction and inhibit the oligomerization of the olefin.

It has been discovered that when utilizing the catalysts which are prepared according to the process of the present invention, the distribution of the reaction products will differ from that which is obtained when utilizing other conventional polymerization catalysts such as Solid Phosphoric Acid. As will hereinafter be shown in greater detail in the examples at the end of the specification, it is possible to obtain a relatively selective reaction product whereby more valuable dimers and trimers of the olefinic hydrocarbon will be recovered. For example, dimethylbutane which is highly desirable as one component in blending motor fuels is obtained in about 12% yield using the reduced titanium chloride-alumina catalyst in contradistinction to a yield of 4.5% of dimethylbutane when using Solid Phosphoric Acid catalyst.

The following examples are given for purposes of illustrating the heterogeneous oligomerization catalysts of the present invention and to their use in oligomerization reactions. However, these examples are given merely for purposes of illustration and are not intended to limit the generally broad scope of the present invention in strict accordance therewith.

EXAMPLE I

In this example a catalyst for the oligomerization of olefinic hydrocarbons was prepared by predrying gamma-alumina at a temperature of 500° C. for a period of 1 hour. A gaseous mixture of hydrogen and titanium tetrachloride vapor was prepared by bubbling hydrogen gas through liquid titanium tetrachloride at ambient temperature and recovering and collecting the resulting gaseous mixture. The spherical gamma-alumina was then placed in a glass tube and the hydrogen-titanium tetrachloride gas mixture was passed through the gamma-alumina column at temperatures of 140° C., 300° C., and 460° C. When the alumina was treated with the hydrogen-titanium tetrachloride gas mixture at 140° C., the color of the alumina became yellow. After treatment at 300° C., the color changed to a very light gray. The catalytic composite was then finished by further reduction in the presence of hydrogen gas at a temperature of 460° C. giving a bluish color to the catalyst. Upon completion of the charge of hydrogen which was at a flow rate of 118 cm/min., the finished catalyst was recovered and sealed under nitrogen.

The catalyst which was prepared according to the above paragraph was then packed in a glass tubular reactor, 30 cc of the catalyst being used for the reaction. Following this, a mixture of propene and helium was passed over the catalyst at a temperature of about 200° C. for a period of about 2 hours. The reaction product was recovered and condensed at a temperature of about −78.5° C. and thereafter subjected to gas chromatographic analysis. The distribution of the product as to $C_6$-$C_7$ carbon atom skeletons, given in percent by weight, which was recovered is set forth in the table below:

| | |
|---|---|
| 2,3-Dimethylbutane | 11.7 |
| 2-Methylpentane | 34.3 |
| 3-Methylpentane | 26.4 |
| n-Hexane | 4.5 |
| Methylcyclopentane | Trace |
| 2,2-Dimethylpentane | 0.5 |
| 2,4-Dimethylpentane | 4.0 |
| 2,2,3-Trimethylbutane | 0.1 |
| 3,3-Dimethylpentane | 0.1 |
| 2-Methylhexane | 4.7 |
| 2,3-Dimethylpentane | 6.5 |
| 1-cis-3-Dimethylcyclopentane | 5.7 |
| 3-Methylhexane | — |
| 1-trans-3-Dimethylcyclopentane | — |
| 1-trans-2-Dimethylcyclopentane | 0.1 |
| 3-Ethylpentane | 0.4 |
| n-Heptane | 0.7 |
| 1-cis-2-Dimethylcyclopentane | — |
| Methylcyclohexane | Trace |

EXAMPLE II

A heterogeneous oligomerization catalyst was prepared by drying 250 cc of one-eighth inch diameter gamma-alumina spheres which had an ABD of about 0.38 at a temperature of 500° C. under a nitrogen gas flow of 2000 cc per minute, said drying being accomplished in a silica glass tube positioned in a vertical furnace. In a second piece of apparatus hydrogen gas was bubbled through liquid titanium tetrachloride at room temperture at a rate of 1000 cc per minute to produce a mixture of hydrogen and titanium tetrachloride vapors. The resulting hydrogen-titanium tetrachloride vapor mixture was passed through the predried gamma-alumina at room temperature until heavy titanium tetrachloride vapors appeared in the exit gas, the initial passage of the vapors being effected in a period of about 2 hours. The furnace temperature was then raised to 140° C. and maintained thereat for a period of about 1.3 hours while passing the hydrogen-titanium tetrachloride vapor mixture through the gamma-alumina at a rate of 500 cc per minute. At the end of this time, the temperature of the furnace was raised to 300° C. and maintained thereat for a period of 1 hour. At the end of the 1-hour period, the temperature was raised to 460° C. and maintained at this temperature for a period of 3.5 hours while passing the hydrogen-titanium tetrachloride vapor mixture over the gamma-alumina at the aforesaid rate of 500 cc per minute. At the end of the 3.5 hours, a hydrogen flow was substituted for the vapor mixture and the further reduction of the catalyst was effected for a period of 0.5 hours. The finished catalyst which was recovered contained 2.3% by weight of titanium and 4.0% by weight of chlorine. Fifty cc of the finished catalyst weighed 15.1 grams.

To effect the oligomerization reaction 50 cc of the catalyst was utilized in an upflow reactor and a feed consisting of 70% 2-butene (45% trans-2-butene and 55% cis-2-butene) and 30% butane was passed over the catalyst under reaction conditions which included a temperature of 140° C., a pressure of 500 pounds per square inch gauge and a liquid hourly space velocity of 3. The reaction product was recovered, condensed at room temperature and subjected to gas chromatographic analysis. It was found that there was about a 55% by weight conversion of 2-butene with a 57.6% by weight selectivity to the dimer. The distribution of the dimer product, given in percent by weight, which was recovered is set forth in the table below:

| Isomers | Wt. % |
|---|---|
| 2,5-Dimethylhexene | 0.5 |
| 2,4-Dimethylhexene | 11.2 |
| 2,3,4-Trimethylpentene | 1.0 |
| 2,3,3-Trimethylpentene | 0.2 |
| 2,3-Dimethylhexene | 14.9 |
| 2-Methylheptene and 3-methyl-3-ethylpentene | 0.3 |
| 3,4-Dimethylhexene | 63.7 |
| 3-Ethylhexene and 3-methylheptene | 4.2 |
| 2,2-Dimethylhexene | 0.5 |
| 3,3-Dimethylhexene | 3.5 |

EXAMPLE III

A catalyst for the oligomerization of olefinic hydrocarbons is prepared by predrying gallium oxide at a temperature of 500° C. for a period of 1 hour. Following this, the gallium oxide is then placed in a flask and a nitrogen-titanium tetrachloride gas mixture which is prepared by bubbling nitrogen gas through liquid titanium tetrachloride at ambient temperature and recovering and collecting the resultant gaseous mixture, is charged to the apparatus and passed over the gallium oxide at a temperature of 140° C. After treatment at a temprature of 140° C. for a period of 1 hour, the temperature is increased to 300° C. while maintaining the flow of the nitrogen-titanium tetrachloride gas over the gallium oxide for a period of 0.5 hours. At the end of this time period, the temperature is increased to 460° C. while changing the gas feed to pure hydrogen gas. The reduction of the titanium tetrachloride with the hydrogen is effected at the aforesaid temperature of 460° C. for a period of 2 hours. At the end of this time, the titanium chloride-gallium oxide catalyst in which the titanium is present in a valence state of less than +4 is recovered and sealed under nitrogen.

The catalyst composite which is prepared according to the above paragraph is then packed in a glass tubular reactor following which a mixture of ethylene and ethane is passed over the catalyst at a temperature of about 200° C. for a period of about 2 hours. The reaction product is recovered by condensation at a temperature of about −80° C. and thereafter is subjected to gas chromatographic analysis. This analysis will disclose the presence of a mixture of dimers and trimers of ethylene.

I claim as my invention:

1. A process for the oligomerization of an olefinic hydrocarbon which contains from 2 to about 6 carbon atoms which comprises oligomerizing said hydrocarbon at oligomerization conditions in the presence of a catalyst which has been prepared by heating a metal oxide which possesses surface hydroxyl groups at a temperature in the range of from about 400° C. to about 600° C., contacting said metal oxide with titanium tetrachloride vapor in a series of steps at progressively higher temperatures within the range of from about 50° C. to about 600° C. to deposit titanium tetrachloride on the metal oxide, and thereafter heating the impregnated metal oxide in contact with hydrogen gas at a temperature in the range of from about 300° C. to about 700° C. to reduce the titanium to a valence state of less than +4, and recovering the resultant oligomer.

2. The process as set forth in claim 1 in which said oligomerization reaction conditions include a temperature in the range of from about ambient to about 250° C. and a pressure in the range of from about atmospheric to about 100 atmospheres.

3. The process as set forth in claim 1 in which said metal oxide which possesses surface hydroxyl groups is an oxide of a metal of Group IIIA of the Periodic Table.

4. The process as set forth in claim 3 in which said metal oxide is a low density, high surface area gamma-alumina.

5. The process as set forth in claim 3 in which said metal oxide is gallium oxide.

6. The process as set forth in claim 3 in which said metal oxide is indium oxide.

7. The process as set forth in claim 1 in which said olefinic hydrocarbon is ethylene.

8. The process as set forth in claim 1 in which said olefinic hydrocarbon is propylene.

9. The process as set forth in claim 1 in which said olefinic hydrocarbon is butene-1.

10. Th process as set forth in claim 1 in which said olefinic hydrocarbon is butene-2.

* * * * *